(12) United States Patent
Garrow et al.

(10) Patent No.: US 8,337,882 B2
(45) Date of Patent: Dec. 25, 2012

(54) PERSONAL STIMULATING WIPING SYSTEMS

(76) Inventors: David Garrow, Scottsdale, AZ (US); Greg Remmers, Fountain Hills, AZ (US)

( * ) Notice: Subject to any disclaimer, the term of this patent is extended or adjusted under 35 U.S.C. 154(b) by 19 days.

(21) Appl. No.: 12/781,792

(22) Filed: May 17, 2010

(65) Prior Publication Data

US 2011/0123595 A1  May 26, 2011

Related U.S. Application Data

(60) Provisional application No. 61/178,997, filed on May 17, 2009.

(51) Int. Cl.
  *A61K 9/70* (2006.01)
  *A61K 33/02* (2006.01)
  *A61P 11/00* (2006.01)
(52) U.S. Cl. ........................................ 424/443; 424/721
(58) Field of Classification Search .................. None
  See application file for complete search history.

(56) References Cited

U.S. PATENT DOCUMENTS

| | | | |
|---|---|---|---|
| 3,325,003 A * | 6/1967 | Bilezerian | 206/494 |
| 3,780,908 A * | 12/1973 | Fitzpatrick et al. | 221/48 |
| 4,314,679 A | 2/1982 | Paul et al. | |
| 4,559,157 A | 12/1985 | Smith et al. | |
| 6,089,947 A | 7/2000 | Green | |
| 6,241,976 B1 | 6/2001 | Esser et al. | |
| 6,482,446 B2 | 11/2002 | Watson | |
| 2004/0242097 A1 | 12/2004 | Hasenoehrl et al. | |
| 2004/0265400 A1 | 12/2004 | Barone, Jr. et al. | |
| 2006/0147507 A1 | 7/2006 | Cammarata | |
| 2007/0122460 A1 | 5/2007 | Daily | |
| 2008/0311166 A1 | 12/2008 | Wimer | |

FOREIGN PATENT DOCUMENTS

| | | |
|---|---|---|
| WO | WO01/07132 | 2/2001 |
| WO | WO0107132 A1 | 2/2001 |

OTHER PUBLICATIONS

McCrory, P. Smelling salts, Br J Sports Med 2006;40:659-660. Downloaded from bjsm.bmj.com on Dec. 1, 2011.*
Brown, L.A., Aromatic Spirit of Ammonia. American Druggist and Pharmaceutical Record, vol. 60, 1912, p. 38.*

* cited by examiner

*Primary Examiner* — Frederick Krass
*Assistant Examiner* — Michael Cohen
(74) *Attorney, Agent, or Firm* — Andrew P. Lahser

(57) ABSTRACT

A wipe to stimulate a person. The wipe is permeated with a smelling salt solution. The smelling salt solution delivers an effective amount of ammonium gas to stimulate the respiratory system of the person. The smelling salt solution delivers an effective amount of alcohol to provide a cooling sensation on the skin. The wipe is contained in a container impermeably to prevent evaporation of the smelling salt solution and to delay transformation of the smelling salts solution to ammonium gas until the container may be opened by the person. Other embodiments and uses are disclosed.

19 Claims, 3 Drawing Sheets

PERSONAL STIMULATING WIPING SYSTEMS

CROSS REFERENCE TO RELATED APPLICATIONS

The present application is related to prior provisional application Ser. No. 61/178,994 filed May 17, 2009 the contents of which are incorporated herein by this reference and are not admitted to be prior art with respect to the present invention by the mention in this cross-reference section.

DETAILED DESCRIPTION

The present Personal Stimulating Wiping Systems will now be discussed in detail with regard to the attached drawing figures, which were briefly described above. In the following description, numerous specific details are set forth illustrating the Applicant's best mode for practicing the Personal Stimulating Wiping Systems and enabling one of ordinary skill in the art to make and use the Personal Stimulating Wiping Systems. It will be obvious, however, to one skilled in the art that the present Personal Stimulating Wiping Systems may be practiced without many of these specific details. In other instances, well-known manufacturing systems, packaging methods, business methods, engineering considerations, and other aspects have not been described in particular detail in order to avoid unnecessarily obscuring this disclosure.

Figure 1:
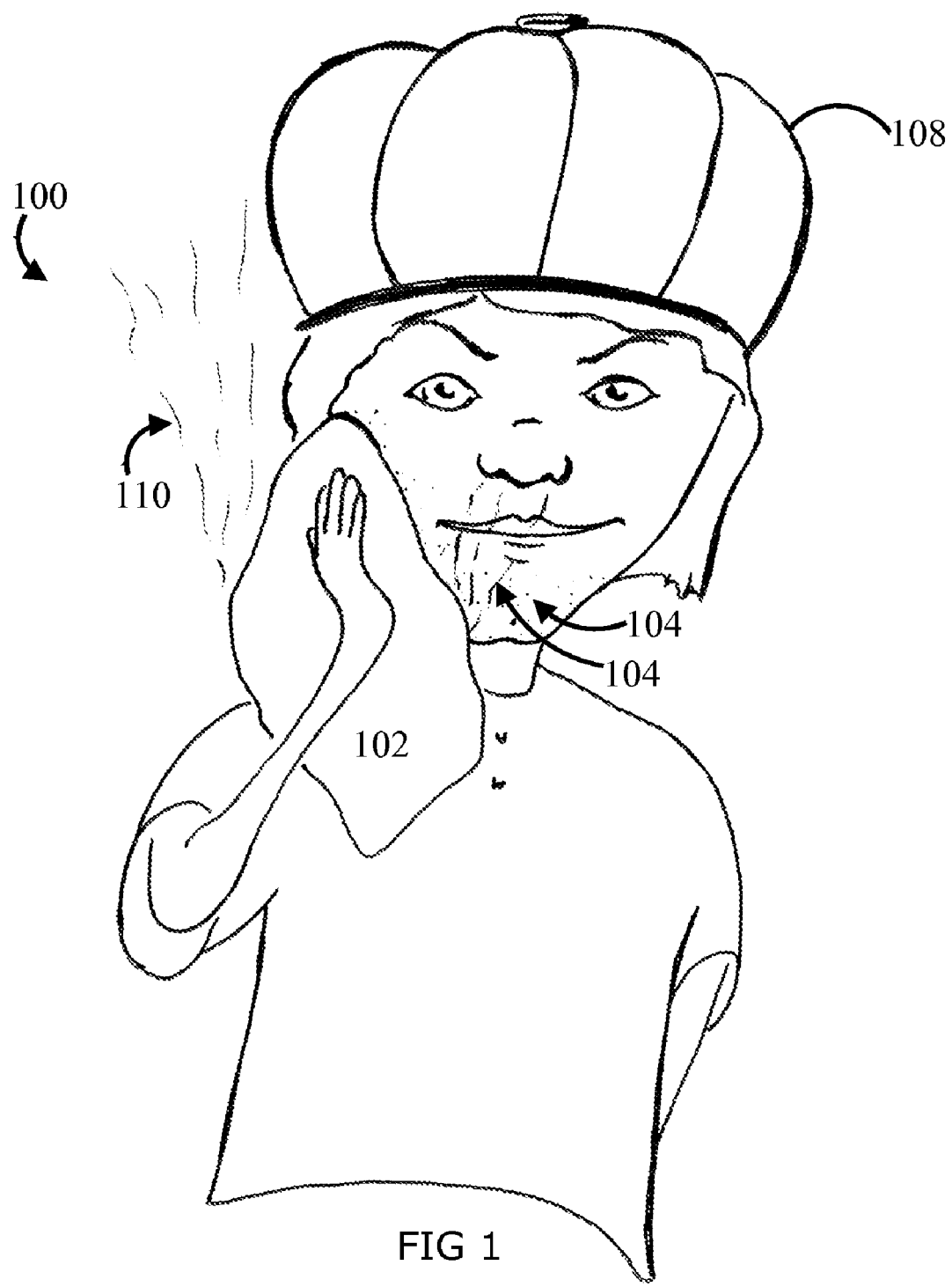
FIG. 1 shows a diagrammatic view illustrating the use of a wipe by wiping along the face, neck or head to deliver cooling alcohol and water and to deliver stimulating ammonia gas and essential oils to the person, according to an embodiment of the present invention.

FIG. 1 shows a diagrammatic view illustrating the process of using wipe 102 by wiping along the face, neck or head to deliver solution 104 of cooling alcohol and water and also to deliver stimulating ammonium gas 106 and essential oils to person 108, according to an embodiment of the present invention. Wipe 102 may be permeated with solution 104, as shown. Wipe 102 may be applied to the face, neck, head or other portion of the body of person 108, as shown. Applying wipe 102 to the person may transfer some of solution 104 to the skin of person 108, as shown. Solution 104 may include a solution of smelling salts or a dilute solution of smelling salts. Solution 104 may include purified water and alcohol that may evaporate after transfer to the skin of person 108, as shown by evaporation 110. Solution 104 may also evaporate directly from wipe 102, which may lower the temperature of wipe 102. Evaporation of solution 104 may cause a cooling sensation or effect for person 108, as shown. Solution 104 may include ammonium salt suspended in the alcohol. The ammonium salt may convert to ammonium gas 106 when wipe 102 becomes unsealed from its container or package and exposed to air. Ammonium gas 106 may be inhaled by person 108, which may create a respiratory stimulating effect, as shown. Wipe 102 may provide absorbency to remove excess sweat from the skin of person 108. Wipe 102 may simultaneously provide evaporative cooling effects, respiratory stimulant effects, and sweat absorbing effects for person 108, as shown.

Wipe 102 may include only enough solution 104 to effectuate the stimulatory effects. Wipe 102 may not include enough solution 104 to allow wipe 102 to excrete solution 104 in a flowing liquid form. By preventing a flowing liquid from wipe 102, accidental consumption of solution 104 by person 108 may be prevented or avoided. By not excreting flowing liquid ammonium or liquid alcohol, this may improve the safety of the use of the smelling salts, because a predetermined effective dosage may be included with the wipe that may be generally safe for use without worry of accidental consumption.

Figure 2:
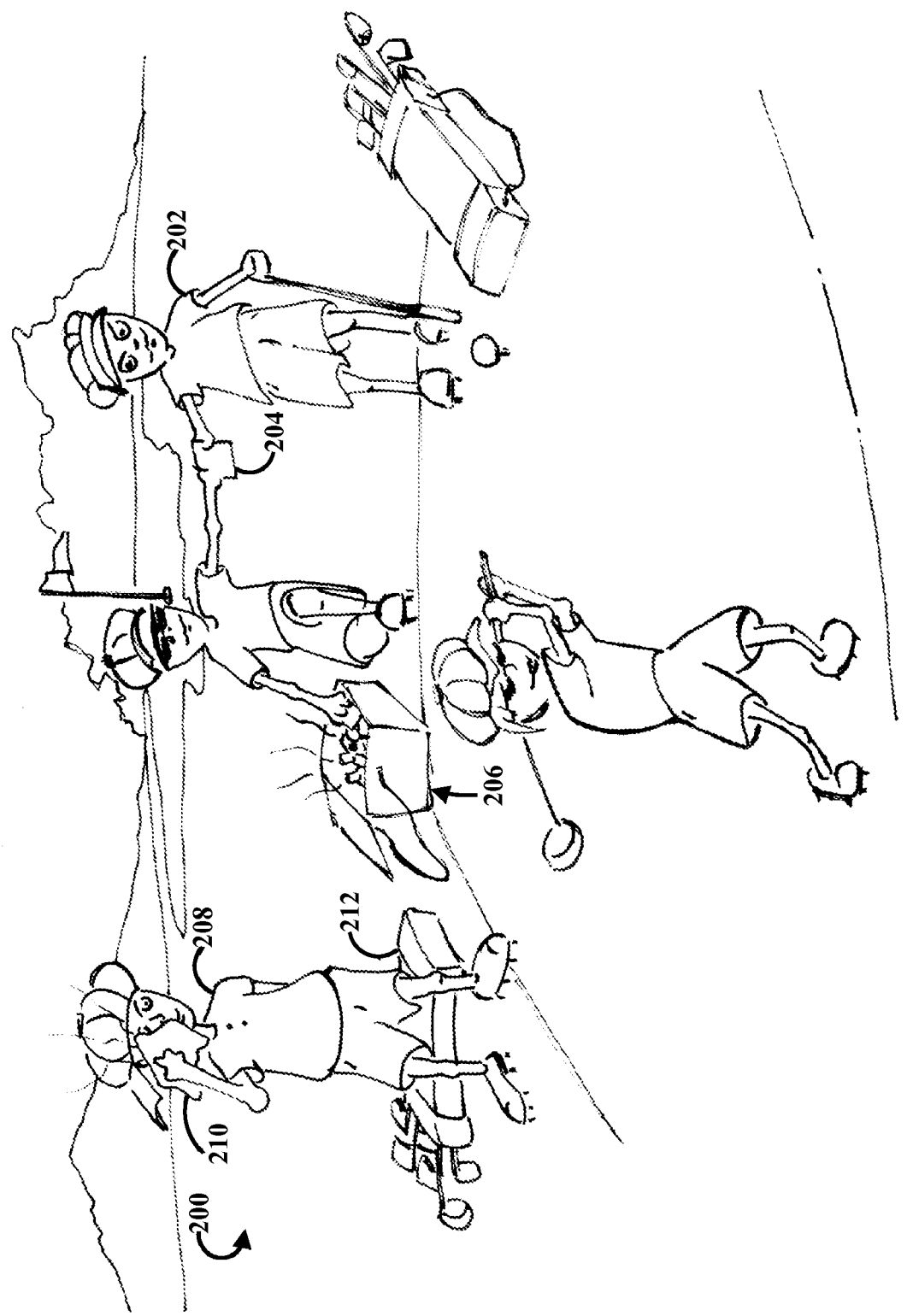
FIG. 2 shows a diagrammatic view illustrating golf athletes using pre-cooled wipes to stimulate and cool the golf athletes during a sporting event, according to an embodiment of the present invention.

FIG. 2 shows a diagrammatic view illustrating athletes 200 playing golf and using pre-cooled wipes to stimulate and cool athletes 200 during a sporting event, according to an embodiment of the present invention. Stimulation may be any type of stimulating effect, such as, for example, cooling the person, stimulating the respiratory system, increasing pace of breathing, mental alerting, focusing or other effects, etc. Stimulating effect may be experienced differently by different persons. Golfer 202 is receiving pre-cooled, sealed wipe 204 which is enclosed in an impermeable container, as shown. Pre-cooled, sealed wipe 204 may have been stored in cooler 206 near ice to lower the temperature of pre-cooled, sealed wipe 204 prior to use, as shown. Other types of external cooling may be used, such as, for example, refrigeration, insulation, dry ice, etc. Pre-cooling the wipes may provide additional stimulating effect by allowing the wipe to absorb additional heat from the person using the wipe.

Golfer 208 has removed wipe 210 by previously tearing open the impermeable package (container) that contained previously sealed wipe 210 that golfer 208 is applying to the face, neck and head, as shown. Wipe 210 may have been previously stored and cooled in cooler 206, as shown. Alternately, wipe 210 may have been previously stored in golf bag 212, where wipe 210 may have stored for several months inside of the durable, polypropylene package (container), as shown. Wipe 210 may provide a stimulating effect for athletes 200 by providing skin cooling, respiratory stimulation, and sweat removal, which athletes 200 may find refreshing or energizing while performing sporting activities, such as golf, football, soccer, basketball, other team sports, other individual sports, etc. Stimulating during or prior to sporting activity may enhance sporting performance.

Stimulating wipes may be useful in other situations where people are likely to be become or be hot or tired, such as, for example, during military actions, during construction activities, outdoor activities, during travel, on airplanes, in hotel rooms, etc. Stimulating wipes may provide comfort or relief from various conditions, such as, for example, headaches, allergies, nausea, fainting, labored breathing, other conditions, etc.

Figure 3:
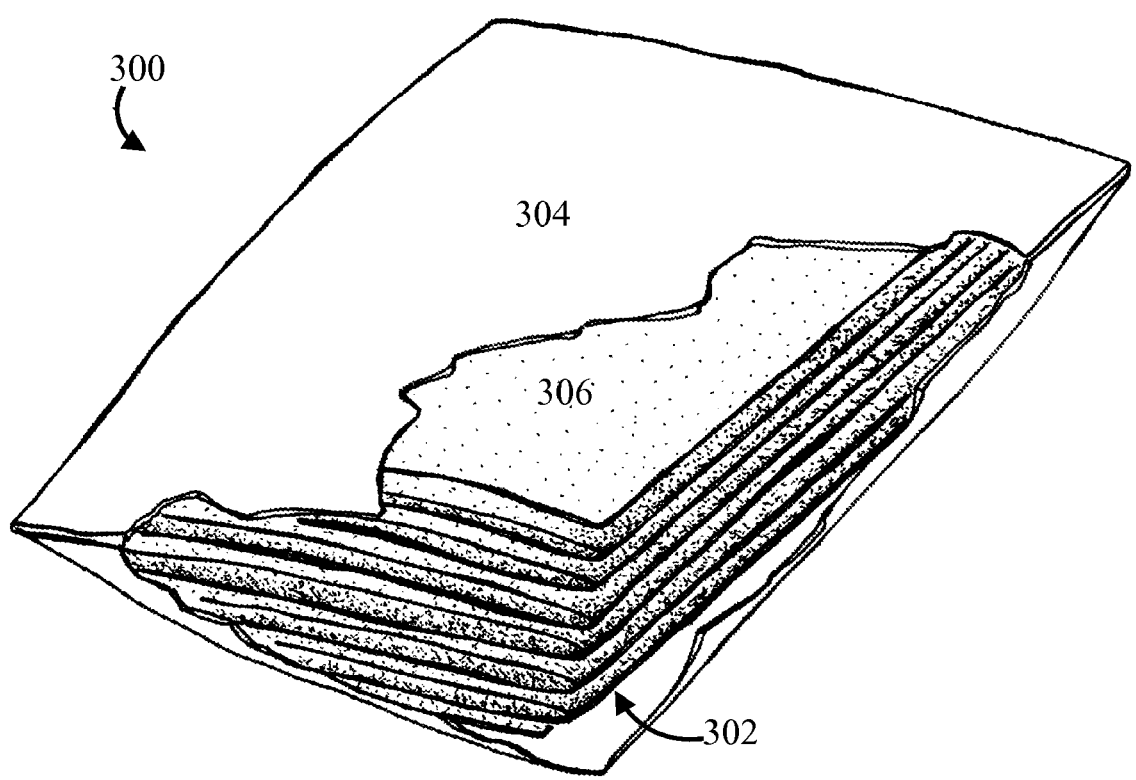
FIG. 3 shows a perspective view illustrating a package containing a stimulating wipe enclosed in an impermeable container, which is shown with a portion of the impermeable container cut away to reveal the folded stimulating wipe inside, according to an embodiment of the present invention.

FIG. 3 shows a perspective view illustrating package 300 that contains stimulating wipe 302 enclosed in an impermeable container 304, which is shown with a portion of impermeable contain 304 cut away to reveal the folded stimulating wipe 302 inside, according to an embodiment of the present invention.

Wipe 302 may be made of any type of absorbent fabric, such as, for example, woven fabric, cotton cloth, disposable gauze, engineered cloth, nonwoven fabric, disposable material, or other types of towels. The type of fabric may be selected based on factors such as absorbency, durability, texture, thermal factors, disposability, advances in fabric technology, economic considerations, manufacturing considerations, packaging considerations, etc. One example of a fabric suitable for use as a wipe may include a wiper manufactured by DuPont having the trade name Sontara with the product number 8838.

Wipe 302 may be sized to fit comfortably in one or two hands. Wipe 102 may be sized 3"×4" (about 12 square inches), 4"×6" (about 24 square inches), 7.5"×11" (about 82.5 square inches), 11"×15" (about 165 square inches), 15"×20" (about 300 square inches), or other various sizes. The size of wipe 302 may be selected based on factors such as absorbency of the fabric, volume of dosage required to effectuate stimulation, economic factors, advances in fabric technology, manufacturing considerations, hand feel, commercial availability, etc. Container 304 may be sized to fit within in a pocket, or purse, sports bag, other equipment used in sporting, etc. Wipe 302 may be folded to fit within container 304, as shown.

Container 304 may be made of any type of impermeable fabric to allow sealing of wipe 302 prior to use and to allow opening of container 304 to permit use of wipe 302. Container 304 may contain impermeably wipe 302, as shown. Container 304 may prevent evaporation of solution 306, as shown. Container 304 may prevent or delay transformation of the suspended ammonium to ammonium gas until container 304 may be opened by a person just prior to intended use. Container 304 may permit removal of wipe 302 so a person can apply wipe 302 near their face, neck, head or other body part.

Examples of impermeable fabric may include poly-propylene, UV resistant material, heat and cold absorbing material, impermeable materials, durable materials designed to survive in sporting environments for a commercial desirable shelf life, inexpensive or disposable materials, etc. Impermeable fabric of container 302 may be selected based upon factors such as economic considerations, advances in fabric technology, manufacturing considerations, impermeability, disposability, shelflife, etc. Container 304 may be permanently sealed and require tearing to open container 304, which may be composed of a tear-able material. In an alternate embodiment, the container may include a closable and reopenable fasteners that provides sealing sufficient to prevent evaporation or transformation of the smelling salt solution, for example, a ziplock with an interlocking groove and ridge that forms a seal when pressed together. In an alternate embodiment, the container may include more than one wipe, for example, two wipes, three wipes, six wipes, twelve wipes, thirty-six wipes, etc. In an alternate embodiment, the container may be a formed plastic container with a openable and resealable lid that contains a bulk pack of wipes, for example, thirty-six wipes, forty-eight wipes, seventy-two wipes, ninety-six wipes, etc.

Solution 306 may be any smelling salt solution to deliver an effective amount of ammonium gas to stimulate the respiratory system. Solution 306 may be any smelling salt solution to deliver an effective amount of alcohol or water to provide a cooling sensation to the skin. Solution 306 may be any smelling salt solution to provide both the stimulatory effect and the cooling effect.

Solution 306 may include ammonium, alcohol, and water. Alternately, Solution 306 may include ammonium, alcohol, water and one or more essential oils. Solution 306 may include ammonium salt suspended in alcohol, such as, for example, ammonium carbonate in ethyl alcohol (ethanol). The concentration of ammonium may be about 0.015%, 0.03%, 0.06%, 0.12%, 0.25%, etc. The concentration of alcohol may be about 0.5%, 1%, 4%, 8%, 16%, 35%, 65%, etc.

Solution 306 may include water at a concentration of about 35%, 50%, 82%, 96%, 97%, 98%, 99%, etc. Ammonium carbonate may convert to ammonium gas whenever it is not sealed in an air tight container.

In another embodiment, Solution 306 may include essential oils, such as, for example, lavender oil, lemon oil terpeneless, myristica oil, spirits of camphor, English lavender oil, ylang ylang, oil of nutmeg, eucalyptus oil, peppermint essential oil, lemongrass essential oil, oil of orris, oil of lavender flowers, extract of violet, etc. Essential oils may provide scent to mask or hide the odor of the ammonium gas or the odor of the alcohol. Essential oils may provide additional stimulation or stimulatory effects. Essential oils may be used in combination, that is, a blend of one or more oils, for example, lavender oil, lemon oil terpeneless, and myristica oil. The concentration of essential oils may be about 0.004%, 0.008%, 0.016%, 0.03%, 0.06%, 0.25%, 0.5%, 1% etc.

In one embodiment of the invention, the solution of smelling salts may include about 97% water, 0.06% ammonium, 2% alcohol, 0.03% essential oils. Selection of the concentration of each component of the solution may consider factors such as, the size and absorbency of the wipe, the effective dosage of the ammonium, the effective dosage of the alcohol, the effective dosage of the water, the effective dosage of the essential oil, the desired strength, manufacturing/packaging considerations, economic factors, etc.

Solution 306 may permeate wipe 302. The quantity or dosage of solution 306 may be selected to deliver an effective amount of ammonium gas to stimulate the respiratory system. The quantity or dosage of solution 306 may be selected to deliver an effective amount of alcohol or water to provide a skin cooling sensation or effect. The quantity or dosage of solution 306 may be selected to be unlikely to cause irritation of the respiratory system of the person. The quantity or dosage of solution 306 may be selected to be unlikely to cause toxicity to the person. The quantity or dosage of solution 306 is less than or equal to the volume of liquid sufficient to completely saturate the wipe so that no liquid may flow from the wipe, thereby preventing the smelling salt solution from being accidentally consumed by the person.

Although applicant has described applicant's best mode and other embodiments of the present Personal Stimulating Wiping Systems, it will be understood that the broadest scope of this invention includes such modifications as diverse application of technology, variance of manufacturing steps, choice of packaging, selection of stimulating effects and strength of those stimulating effects, type of sport, intended use, and other aspects, etc. Such scope is limited only by the below claims as read in connection with the above specification. Further, many other advantages of applicant's invention will be apparent to those skilled in the art from the detailed descriptions and the claims.

What is claimed is:

1. A method to stimulate a person comprising the steps of:
permeating a wipe with a dilute smelling salt solution, wherein the dilute smelling salt solution comprises water at a concentration of about 35% to about 99% by volume; alcohol at a concentration of about 0.5% to about 65% by volume; ammonia at a concentration of about 0.015% to about 0.12% by volume; and one or more essential oils at a concentration of about 0.004% to about 1% by volume;
containing the wipe inside an impermeable container to prevent evaporation of the dilute smelling salt solution and to delay transformation of the dilute smelling salt solution to ammonia gas until the impermeable container may be opened by the person;

removing the wipe from the impermeable container; and
after removal from the impermeable container, applying said wipe to the person to deliver an effective amount of ammonia gas to stimulate the respiratory system of the person and to deliver an effective amount of alcohol to provide a cooling sensation on the skin.

2. The method of claim 1 wherein:
the wipe comprises nonwoven, engineered cloth.

3. The method of claim 1 wherein:
the dilute smelling salt solution comprises 0.004% and to 0.5% peppermint oil by volume.

4. The, method of claim 1 wherein:
the wipe comprises disposable material.

5. The, method of claim 1 wherein:
the wipe comprises an area from 82.5 square inches to about 300 square inches.

6. The, method of claim 1 wherein:
the dilute smelling salt solution consists essentially of
water at a concentration of 96% to 99% by volume;
alcohol at a concentration of 1% to 4% by volume; and
ammonia at a concentration of 0.015% to 0.12% by volume.

7. The method of claim 1 wherein:
the dilute smelling salt solution consists essentially of
water at a concentration of 96% to 99% by volume;
alcohol at a concentration of 1% to 4% by volume;
ammonia at a concentration of 0.015% to 0.12% by volume; and
one or more essential oils at a concentration of 0.004 to 0.06% by volume.

8. The, method of claim 1 wherein:
the dilute smelling salt solution comprises a concentration of ammonia insufficient to irritate the respiratory system of the person.

9. The, method of claim 1 wherein:
the container comprises tear-able, polypropylene material.

10. The, method of claim 1 wherein:
the container comprises tear-able, polypropylene material permanently sealed around the exactly one wipe and whereby the container must be torn to open and reveal the exactly one wipe.

11. The, method of claim 1 wherein:
the dosage of dilute smelling salt solution is less than or equal to the dosage sufficient to completely saturate the wipe so that no dilute smelling salt solution may flow from the wipe, thereby preventing the dilute smelling salt solution from being accidentally consumed by the person.

12. The method of claim 1 wherein:
the wipe comprises a disposable, nonwoven, engineered cloth of an area from about 82.5 square inches to about 300 square inches;
the container comprises tear-able, polypropylene material;
the dilute smelling salt solution consists essentially of
water at a concentration of 96% to 99% by volume;
alcohol at a concentration of 1% to 4% by volume; and
ammonia at a concentration of 0.015% to 0.12% by volume;
the dilute smelling salt solution includes a concentration of ammonia insufficient to irritate the respiratory system of the person; and
the dosage of dilute smelling salt solution is less than or equal to the dosage sufficient to completely saturate the wipe so that no dilute smelling salt solution may flow from the wipe, thereby preventing the dilute smelling salt solution from being accidentally consumed by the person.

13. The method of claim 1 wherein:
the wipe comprises a disposable, nonwoven, engineered cloth of an area from about 82.5 square inches to about 300 square inches;
the container comprises tear-able, polypropylene material;
the dilute smelling salt solution consists essentially of
water at a concentration of 96% to 99% by volume;
alcohol at a concentration of 1% to 4% by volume;
ammonia at a concentration of 0.015% to 0.12% by volume; and
peppermint oil at a concentration of 0.004 to 0.06% by volume;
the dilute smelling salt solution includes a concentration of ammonia insufficient to irritate the respiratory system of the person; and
the dosage of dilute smelling salt solution is less than or equal to the dosage sufficient to completely saturate the wipe so that no dilute smelling salt solution may flow from the wipe, thereby preventing the dilute smelling salt solution from being accidentally consumed by the person.

14. The, method of claim 1 wherein:
the wipe comprises a disposable, nonwoven, engineered cloth of an area from about 82.5 square inches to about 300 square inches;
the container comprises tear-able, polypropylene material;
the dilute smelling salt solution comprises
water at a concentration of about 35% to about 99% by volume,
alcohol at a concentration of about 0.5% to about 65% by volume,
ammonium at a concentration of about 0.015% to about 0.12% by volume, and
essential oil at a concentration of about 0.004% to about 1% by volume;
the dilute smelling salt solution includes a concentration of ammonium insufficient to irritate the respiratory system of the person; and
the dosage of dilute smelling salt solution is less than or equal to the dosage sufficient to completely saturate the wipe so that no dilute smelling salt solution may flow from the wipe, thereby preventing the dilute smelling salt solution from being accidentally consumed by the person.

15. A method to stimulate or to cool a person comprising the steps of:
providing a dilute smelling salt solution to deliver an effective amount of ammonia gas to stimulate the respiratory system of the person, and to deliver an effective amount of alcohol to provide a cooling sensation on the skin wherein the dilute smelling salt solution comprises water at a concentration of about 35% to about 99% by volume; alcohol at a concentration of about 0.5% to about 65% by volume; ammonia at a concentration of about 0.015% to about 0.12% by volume; and one or more essential oils at a concentration of about 0.004% to about 1% by volume;
dosing a wipe with a dosage of the dilute smelling salt solution less than or equal to the dosage sufficient to completely saturate the wipe so that no liquid may flow from the wipe, wherein the wipe comprises an area from 82.5 square inches to about 300 square inches, thereby preventing the dilute smelling salt solution from being accidentally consumed by the person; and
having the person apply the dilute smelling salt solution to the face, head or neck by applying the wipe directly to the face, head, or neck.

16. The method of claim 15 wherein:
the dilute smelling salt solution consists essentially of
water at a concentration of 96% to 99% by volume;
alcohol at a concentration of 1% to 4% by volume; and
ammonia at a concentration of 0.015% to 0.12% by volume.

17. The method of claim 15 wherein:
the dilute smelling salt solution consists essentially of
water at a concentration of 96% to 99% by volume;
alcohol at a concentration of 1% to 4% by volume;
ammonia at a concentration of 0.015% to 0.12% by volume; and
one or more essential oils at a concentration of 0.004 to 0.06% by volume.

18. The method of claim 15 wherein:
the dilute smelling salt solution comprises
water at a concentration of about 35% to about 99% by volume;
alcohol at a concentration of about 0.5% to about 65% by volume;
ammonia at a concentration of about 0.015% to about 0.12% by volume; and
one or more essential oil at a concentration of about 0.004% to about 1% by volume.

19. The, method of claim 18 comprising:
wherein the wipe comprises a disposable, nonwoven, engineered cloth of an area from about 12 square inches to about 300 square inches;
wherein the dilute smelling salt solution comprises
water at a concentration of about 35% to about 99% by volume,
alcohol at a concentration of about 0.5% to about 65% by volume,
ammonia at a concentration of about 0.015% to about 0.12% by volume,
one or more essential oil at a concentration of about 0.004% to about 1% by volume; and
wherein the dilute smelling salt solution includes a concentration of an ammonia insufficient to irritate the respiratory system of the person.

* * * * *